United States Patent
Nisbet

(10) Patent No.: US 9,023,383 B2
(45) Date of Patent: May 5, 2015

(54) WOUND DRESSING MATERIALS

(75) Inventor: Lorraine Nisbet, Skipton (GB)

(73) Assignee: KCI USA, Inc., San Antonio, TX (US)

(*) Notice: Subject to any disclaimer, the term of this patent is extended or adjusted under 35 U.S.C. 154(b) by 305 days.

(21) Appl. No.: 13/318,938

(22) PCT Filed: May 5, 2010

(86) PCT No.: PCT/GB2010/000883
§ 371 (c)(1),
(2), (4) Date: Jan. 26, 2012

(87) PCT Pub. No.: WO2010/128281
PCT Pub. Date: Nov. 11, 2010

(65) Prior Publication Data
US 2012/0135062 A1 May 31, 2012

(30) Foreign Application Priority Data
May 6, 2009 (GB) .................. 0907808.0

(51) Int. Cl.
| A61L 15/16 | (2006.01) |
| A61L 15/00 | (2006.01) |
| A61K 31/24 | (2006.01) |
| A61K 38/48 | (2006.01) |
| A61L 15/44 | (2006.01) |
| A61L 15/32 | (2006.01) |

(52) U.S. Cl.
CPC .............. *A61L 15/44* (2013.01); *A61L 15/32* (2013.01); *A61L 2300/214* (2013.01); *A61L 2300/40* (2013.01); *A61L 2300/428* (2013.01); *A61L 2300/45* (2013.01)

(58) Field of Classification Search
None
See application file for complete search history.

(56) References Cited

U.S. PATENT DOCUMENTS

| 5,149,829 A | | 9/1992 | Seib et al. |
| 5,296,500 A | | 3/1994 | Hillebrand |
| 5,804,168 A | * | 9/1998 | Murad ................ 424/401 |
| 6,166,084 A | * | 12/2000 | Bloor ................. 514/613 |

FOREIGN PATENT DOCUMENTS

| GB | 2450477 A * | 12/2008 |
| WO | 95/00136 A1 | 1/1995 |
| WO | 02/01954 A1 | 1/2002 |
| WO | 2008/155512 A2 | 12/2008 |

OTHER PUBLICATIONS

Enoch et al. Basic science of wound healing, Surgery; 26:2 (2007) 31-37.*
Mustoe, Understanding chronic wounds: a unifying hypothesis on their pathogenesis and implications for therapy, Am J of Surgery, 187 (Suppl to May 2004) 65S-70S.*
See Li et al. Pathophysiology of acute wound healing, Clinics in Dermatology (2007) 25, 9-18.*
International Search Report issued in International Application No. PCT/GB2010/000883.

* cited by examiner

*Primary Examiner* — Michael G Hartley
*Assistant Examiner* — Nabila Ebrahim

(57) ABSTRACT

A wound dressing material comprising: a wound dressing carrier, N-acetyl cysteine or a salt or derivative thereof, and a stabilized ascorbate. Suitably, the stabilized ascorbate comprises an ascorbate-2-polyphosphate. Also provided are wound dressing comprising the materials, methods of treatment with the materials, and methods of making the materials.

20 Claims, 3 Drawing Sheets

WOUND DRESSING MATERIALS
> 
> ## CROSS-REFERENCE TO RELATED APPLICATIONS
> 
> The present application is a U.S. National Stage of International Application No. PCT/GB2010/000883, filed 5 May 2010, which claims priority to GB Patent Application No. 0907808.0, filed 6 May 2009, the contents of which are hereby incorporated by reference in their entirety.
> 
> The present invention relates to wound dressing materials comprising, in combination, N-acetyl cysteine or salts or derivatives thereof (NAC) and a salt or a derivative of ascorbic acid. The present invention also relates to the use of such materials for the treatment of wounds, in particular chronic wounds.
> 
> N-acetyl cysteine(N-acetyl-3-mercaptoalanine, L-Alpha-acetamido-beta-mercaptopropionic Acid, N-acetyl-L-cysteine, hereinafter referred to as NAC) is a derivative of the naturally occurring amino acid N-cysteine. NAC is a sulfhydryl group donor and is therefore considered an antioxidant, and as such it is commonly used as a stabilizer compound on pharmaceutical preparations. NAC is also available in pharmaceutical compositions for the treatment of paracetamol (acetaminophen) overdose, and as a mucolytic in the treatment of dry eye syndromes, chronic bronchitis and cystic fibrosis.
> 
> WO95/00136 describes the use of NAC or pharmaceutically acceptable salts or derivatives thereof for the topical or systemic treatment of hyperkeratosis or disorders mediated by proteinases. The specific diseases mediated by proteinases cited in this application are lichen planus, bullous diseases and mouth ulcers. The compositions may optionally contain ascorbic acid as a preservative.
> 
> WO93/04669 describes compositions containing NAC and its derivatives for regulating skin wrinkles and/or skin atrophy. The compositions may optionally contain from 0.1% to 10% of ascorbic acid or salts thereof as an anti-oxidant/radical scavenger.
> 
> U.S. Pat. No. 4,708,965 describes the use of NAC and its derivatives for the treatment of herpes eruptions and ulcers. This use is based on the ability of NAC to interfere with leukotriene synthesis.
> 
> U.S. Pat. No. 4,724,239 describes treatment of chemical ulcers caused by leukotriene production, the treatment being effected with compositions containing NAC.
> 
> EP-A-0849951 describes the use of a N-acetyl cysteine or a pharmaceutically acceptable salt or derivative thereof for the treatment or prophylaxis of chronic wounds. However, there is no suggestion to use the NAC in combination with ascorbic acid or a derivative thereof.
> 
> Ascorbic acid (Vitamin C) is a well known acidulent, vitamin, and antioxidant substance. The use of ascorbic acid in wound dressings has been studied. See, for example, WO-A-0201954, U.S. Pat. No. 4,711,780 or EP-A-0172326.
> 
> ## SUMMARY OF THE INVENTION
> 
> The present inventors have found that NAC and ascorbic acid derivatives, in combination, exhibit synergistic properties that are likely to make the combination especially suitable for use in wound dressings, especially for the treatment of chronic wounds.
> 
> Accordingly, in a first aspect the present invention provides a wound dressing material comprising: a wound dressing carrier, N-acetyl cysteine or a salt or derivative thereof; and a stabilized ascorbate.
> 
> In a further aspect, the present invention provides a wound dressing comprising a wound dressing material according to the invention.
> 
> In a further aspect, the present invention provides a method of treatment of a chronic wound comprising applying thereto an effective amount of a dressing material according to the invention.
> 
> In a further aspect, the present invention provides a material comprising a wound dressing carrier, N-acetyl cysteine or a salt or derivative thereof; and ascorbic acid or a salt or derivative thereof, for use in the treatment of a chronic dermal wound.
> 
> In a further aspect, the present invention provides a method of making a wound dressing material comprising the steps of (a) dispersing one or more medically acceptable polymeric materials, N-acetyl cysteine or a salt or derivative thereof, and ascorbic acid or a salt or derivative thereof in an aqueous solvent to form an aqueous dispersion; and (b) freeze-drying or solvent-drying the aqueous dispersion to produce the wound dressing material.
> 
> ## DETAILED DESCRIPTION OF THE INVENTION
> 
> The term "derivative" refers to a chemical derivative that exhibits similar activity to the parent compound, and/or to a prodrug that is cleaved in vivo to the parent, active compound.
> 
> Medically-acceptable salts of the active compounds herein include, but are not limited to, sodium, potassium, magnesium, calcium, lithium, rubidium strontium, aluminum, boron, silicon and zinc salts of the active compounds, or salts formed with cations of nitrogenous bases such as ammonia, D-glucosamine or ethylenediamine.
> 
> As used herein, "effective amount" means an amount of compound or composition sufficient to significantly induce a positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular medically-acceptable carrier utilized, and like factors within the knowledge and expertise of the attending physician.
> 
> The first active component of the wound dressings according to the present invention is N-acetyl Cysteine (NAC), or any medically acceptable salt or derivative thereof, optionally including cysteine itself. However, suitably the NAC derivative is not cysteine. Most suitably this component of the composition consists essentially of NAC itself. Suitable derivatives are described, for example, in WO95/00136 and WO93/04669. For example, a medically acceptable derivatives of WO93/04669 have Formula I:

$$R^1-CO-NH-CH(COOR^3)-CH_2-S-R^2 \qquad (I)$$

or a medically-acceptable salt thereof, wherein:
$R^1$ is selected from the group consisting of nil and a $C_1$-$C_{18}$ alkyl, preferably $C_1$-$C_7$, more suitably $C_1$-$C_3$, more suitably still $C_1$ alkyl.
$R^2$ is selected from the group consisting of nil, —H, $C_1$-$C_{18}$ alkyl and $R^4CO$—; suitably H or $C_1$-$C_{18}$ alkyl; more suitably H. In one embodiment, $R^2$ is suitably a $C_1$-$C_{18}$ alkyl, more suitably $C_1$-$C_7$, more suitably $C_1$-$C_3$, more suitably still $R^3$ is selected from the group consisting of —H, and $C_1$-$C_{18}$ alkyl, suitably —H. In one embodiment, $R^3$ is suitably a $C_1$-$C_{18}$ alkyl, more suitably $C_1$-$C_7$, more suitably $C_1$-$C_3$, more suitably still $C_1$ $R^4$ is a $C_1$-$C_{18}$ alkyl; suitably $C_1$-$C_7$; more suitably $C_1$-$C_3$; more suitably still $C_1$.

In another embodiment, both $R^1$ and $R^2$ are nil and the carbonyl carbon and the sulfur adjacent $R^1$ and $R^2$, respectively, are covalently bonded to form a cyclic ring. Otherwise, both $R^1$ and $R^2$ are other than nil.

Suitably, the materials of the present invention comprise NAC itself, or a medically acceptable salt thereof.

The materials according to the present invention suitably comprise from about 0.1% to about 20% of the NAC or salts or derivatives thereof, more suitably from about 1% to about 10%, for example from about 2% to about 8%, typically about 6% by weight based on the total weight of the composition.

The second active component of the wound dressings according to the present invention is a stabilized ascorbate.

The formulation of ascorbic acid itself presents difficulties because it is easily oxidized. Upon storage or exposure to light, oxygen, moisture and/or high temperature, ascorbic acid undergoes rapid degradation. It is unstable in aqueous solution, even under neutral pH and at room temperature. It also reacts with certain minerals, such as iron and copper salts, which contribute to a more rapid degradation. Therefore, the materials of the present invention suitably are substantially free of ascorbic acid itself, for example they suitably comprise less than about 1 wt. % of the free acid, and preferably also less than about 1 wt. % of ascorbic acid salts.

In order to overcome the problem of the lack of stability of ascorbic acid and its soluble salts, the materials of the present invention suitably do not comprise such materials. Instead, the materials of the present invention comprise ascorbate derivatives that are more stable, referred to herein as "stabilized ascorbate". Generally, the stabilized ascorbate exhibits lower antioxidant activity that free ascorbic acid, for example as determined by the rate at which is reduces the absorbance of a $10^{-4}$M solution of diphenylpicrylhydrazyl (DPPH), or as measured by its ability to inhibit the oxidation of ABTS (2,2'-azino-di-[3-ethylbenzthiazoline sulphonate]) by a peroxidase.

According to one approach, stabilization of ascorbic acid and its derivatives is achieved after entrapment into cyclodextrins, zeolites or liposomes.

Another approach consists of stabilizing ascorbic acid by derivatization of its enediol function. Ascorbic acid in its lactone form has four hydroxyl groups at carbons 2, 3, 5 and 6. These hydroxyl groups have different chemical activities: the 2- and 3-hydroxyl groups, together with the double bond connecting carbons 2 and 3, form an enediol system that is very sensitive to oxidation and is responsible for the oxidative degradation of ascorbic acid, whereas the 5- and 6-hydroxyl groups form a rather stable-diol system. Common derivatization of ascorbic acid converts the hydroxyl groups to alkyl-, acyl-, sulfo-, or phosphoryl-containing groups, which also affect the solubility of ascorbic acid in water or in oils. Known ascorbic acid derivatives fall into two main groups, water-soluble and oil-soluble ascorbic acid derivatives. Stabilization of ascorbic acid by derivatization of its enediol function at the 2-position has been attempted by preparation of the water-soluble derivatives L-ascorbic acid 2-phosphate or L-ascorbic acid 2-sulfate salts. For example, magnesium L-ascorbic acid-2-phosphate (MAP) is a water-soluble, stable, non-poisonous and non-irritating derivative. Among the known oil-soluble derivatives the best known is 6-ascor-byl palmitate. Suitably, the materials of the present invention comprise water-soluble ascorbic acid derivatives.

U.S. Pat. Nos. 4,647,672 and 5,149,829 describe stable, 2-polyphosphorylated species of L-ascorbic acid and its stereoisomers. The 2-polyphosphate esters of L-ascorbate described in these patents have proved to be an excellent source of vitamin C for nutrition, particularly in aquatic feeds, on account of their stability, low solubility and high bioavailability. The ascorbate 2-polyphosphate esters are commercially available from Roche under the Registered Trade Mark STAY-C.

Suitably, the wound dressing material of the present invention comprises an ascorbic acid derivative selected from ascorbate 2-phosphate or polyphosphate compound, Trisodium-L-ascorbyl-2-monophosphate; 2-Phospho-L-ascorbic acid trisodium salt, Magnesium Ascorbyl Phosphate (MAP), L-Ascorbic acid mono(dihydrogen phosphate) magnesium salt, Magnesium L-ascorbic acid-2-phosphate, trisodium-L-ascorbyl-2-polyphosphate, or a mixture thereof.

Ascorbate 2-polyphosphates (AZP) and derivatives thereof suitable for use in the present invention have the Formula I:

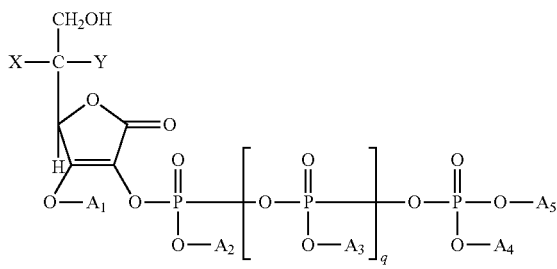

where X and Y are different respectively taken from the group consisting of —H and —OH, and q normally ranges from 1 to 4; in addition $A_1$, $A_2$, $A_3$, $A_4$ and $A_5$ are respectively taken from the group consisting of hydrogen and salt-forming cations. The materials of the present invention may comprise mixtures of more than one compound of Formula I.

The ascorbate 2-polyphosphates useful herein encompass not only the free acid forms but also the salts thereof (e.g., alkali metal, alkali earth, ammonium or C1-C10 alkylammonium salts). The ascorbate may be any stereoisomer, or mixtures thereof. L-ascorbate 2-polyphosphates are preferred. A suitable ascorbate 2-polyphosphate comprises the triphosphate, suitably L-ascorbate 2-triphosphate. Suitably, at least about 50 wt. % of the ascorbate in the dressing is the triphosphate, and suitably it consists essentially of the triphosphate. Suitable methods of preparation and purification of the ascorbate 2-polyphosphates are described in U.S. Pat. Nos. 4,647,672 and 5,149,829.

The materials according to the present invention suitably comprise from about 0.1% to about 20% of the stabilized ascorbate, more suitably from about 1% to about 10%, for example from about 2% to about 8%, typically about 6% by weight based on the total weight of the composition.

Suitably, the weight ratio of the NAC or salts or derivatives thereof to the stabilized ascorbate in the materials of the present invention is in the range of from about 1:10 to about 10:1, more suitably from about 1:4 to about 4:1, for example from about 1:2 to about 2:1. Suitably, the molar ratio of the NAC or salts or derivatives thereof to the stabilized ascorbate in the materials of the present invention is in the range of from about 1:10 to about 10:1, more suitably from about 1:4 to about 4:1, for example from about 1:2 to about 2:1.

Suitably, the materials according to the present invention provide sustained release of the NAC and ascorbate into the wound in use. Suitably, the materials according to the present invention provide a concentration of NAC (or derivatives or salts thereof) and ascorbate (or derivatives or salts thereof) in wound fluid of from about 0.1 mM to about 10 mM, more suitably from about 0.5 mM to about 8 mM, for example from about 1 mM to about 6 mM.

The term "wound dressing carrier", as used herein, means one or more compatible solid, semi-solid or liquid filler diluents or microencapsulating substances which are suitable for administration to a human or higher animal. Wound dressing carriers must be of sufficiently high purity and sufficiently low toxicity to render them suitable for administration to the human or animal being treated. A safe and effective amount of carrier is suitably from about 50% to about 99% by weight, more suitably from about 80% to about 98%, for example from about 85% to about 95% by weight, of the material.

Suitably, the wound dressing carrier is bioabsorbable. The term "bioabsorbable" refers to a material that is fully degraded and absorbed in vivo in the mammalian body. Suitably, the materials comprise, or consist essentially of, one or more biopolymers. That is to say, polymers of biopolymer origin, optionally chemically modified and/or cross-linked.

Suitably, the wound dressing carrier is a solid carrier. For example the solid carrier may be a woven or nonwoven fabric, a foam, or a freeze-dried or solvent-dried sponge. In other embodiments, the solid carrier may be a film of a medically acceptable polymer, such as a hydrogel polymer, optionally containing a plasticiser to improve flexibility. The active agents may be coated on, or dispersed in, the carrier.

The carrier is usually not water soluble, but it may be water swellable. The polymers forming the carrier may be bioabsorbable or non-bioabsorbable. Suitable non-bioabsorbable polymers include alginates. Suitable bioabsorbable polymers include those selected from the group consisting of collagens, bioabsorbable cellulose derivatives such as oxidized celluloses, galactomannans such as guar or xanthan, glycosaminoglycans such as cross-linked hyaluronates, and mixtures thereof.

Suitably, the carrier in the wound dressing material of the invention comprises or consists essentially of a freeze-dried or solvent-dried polymer sponge having the active agents dispersed therein.

In certain embodiments the polymeric sponge matrix comprises (and may consist essentially of) a solid bioabsorbable polymer selected from the group consisting of collagens, chitosans, oxidized celluloses, and mixtures thereof.

Oxidized cellulose is produced by the oxidation of cellulose, for example with dinitrogen tetroxide as described in U.S. Pat. No. 3,122,479. This process converts primary alcohol groups on the saccharide residues to carboxylic acid group, forming uronic acid residues within the cellulose chain. The oxidation does not proceed with complete selectivity, and as a result hydroxyl groups on carbons 2 and 3 are occasionally converted to the keto form. These ketone units introduce an alkali labile link, which at pH7 or higher initiates the decomposition of the polymer via formation of a lactone and sugar ring cleavage. As a result, oxidized cellulose is biodegradable and bioabsorbable under physiological conditions.

A suitable oxidized cellulose for practical applications is oxidized regenerated cellulose (ORC) prepared by oxidation of a regenerated cellulose, such as rayon. It has been known for some time that ORC has haemostatic properties, and that application of ORC fabric can be used to reduce the extent of post-surgical adhesions in abdominal surgery.

Chitin is a natural biopolymer composed of N-acetyl-D-glucosamine units. Chitin may be extracted from the outer shell of shrimps and crabs in known fashion. The chitin is then partially deacetylated, for example by treatment with 5M-15M NaOH, to produce chitosan. Complete deacetylation of the chitin is not a practical possibility, but suitably the chitosan is at least 50% deacetylated, more suitably at least 75% deacetylated. Chitosan has been employed for wound treatment in various physical forms, e.g. as a solution/gel; film/membrane; sponge; powder or fiber. Chitosan in the free base form is swellable but not substantially soluble in water at near-neutral pH, but soluble in acids due to the presence of ammonium groups on the chitosan chain. The solubility of the chitosan may be reduced by cross-linking, for example with epichlorhydrin. Typically, the average molecular weight of the chitosan as determined by gel permeation chromatography is from about 105 to about 106.

The collagen useful in the polymeric sponge materials according to the present invention may be any collagen, including Type I or Type II or Type III collagen, natural fibrous collagen, atelocollagen, partially hydrolysed collagens such as gelatin, and combinations thereof. Natural fibrous collagen, for example of bovine origin, is suitable. For example, the collagen prepared from bovine hide is a combination of Type I collagen (85%) and Type III collagen (15%).

In certain embodiments of the present invention, the oxidized cellulose is complexed with collagen and/or chitosan to form sponges of the kind described in WO98/00180, WO98/00446 or WO2004/026200. For example, the oxidized cellulose may be in the form of milled ORC fibres that are dispersed in a freeze-dried collagen or chitosan sponge. This provides for certain therapeutic and synergistic effects arising from the complexation with collagen.

In particular embodiments, the polymeric sponge carrier comprises (and may consist essentially of) a mixture of: (a) collagen and/or chitosan; and (b) oxidized regenerated cellulose, for example in a dry weight ratio range of from about 90:10 to about 10:90 of collagen/chitosan:ORC, suitably from about 75:25 to about 25:75, and particularly from about 60:40 to about 40:60.

The wound dressing material may also comprise up to 20% by weight, suitably less than 10% by weight of water. The material may also contain 0-40% by weight, suitably 0-25% by weight of a plasticiser, suitably a polyhydric alcohol such as glycerol.

The material may also comprise 0-10% by weight, suitably 0-5% by weight of one or more therapeutic wound healing agents, such as non-steroidal anti-inflammatory drugs (e.g. acetaminophen), steroids, antibiotics (e.g. penicillins or streptomycins), antiseptics (e.g. silver sulfadiazine or chlorhexidine), or growth factors (e.g. fibroblast growth factor or platelet derived growth factor). All of the above percentages are on a dry weight basis.

The preferred antimicrobial agent for inclusion in the wound dressing materials according to the present invention is silver (as silver ions and metallic silver), suitably in an amount of from about 0.01 wt % to about 5 wt. %, more suitably from about 0.05 wt % to about 1 wt. %, and most suitably about 0.1 wt. % to about 0.3 wt. %. In preferred embodiments, the silver may be complexed to the polymeric carrier material. The term "complex" refers to an intimate mixture at the molecular scale, suitably with ionic or covalent bonding between the silver and the polymer. The complex suitably comprises a salt formed between an anionic polymer or collagen and $Ag^+$. Suitable wound dressing sponges comprising silver are described in more detail in WO2004/024197.

Suitably, the material according to the present invention will absorb water or wound fluid and hence become wet, swell or become a gelatinous mass but will not spontaneously dissolve or disperse therein. That is to say, it is hydrophilic but has a solubility of suitably less than about 1 g/liter in water at 25° C. Low solubility renders such materials especially suitable for use as wound dressings to remove reactive oxygen species from the wound fluid.

The wound dressing material is typically in sheet form, for example having an area of from about 1 $cm^2$ to about 400 $cm^2$, in particular from about 2 $cm^2$ to about 100 $cm^2$. The basis weight of the sheet is typically from about 100 $g/m^2$ to about 5000 $g/m^2$, for example from about 400 $g/m^2$ to about 2000 $g/m^2$.

The wound dressing material according to the present invention is suitably sterile and packaged in a microorganism-impermeable container.

In a further aspect, the present invention provides a wound dressing comprising a wound dressing material according to the invention.

The wound dressing is suitably in sheet form and comprises an active layer of the material according to the invention. The active layer would normally be the wound contacting layer in use, but in some embodiments it could be separated from the wound by a liquid-permeable top sheet. Suitably, the area of the active layer is from about 1 $cm^2$ to about 400 $cm^2$, more suitably from about 4 $cm^2$ to about 100 $cm^2$.

Suitably, the wound dressing further comprises a backing sheet extending over the active layer opposite to the wound facing side of the active layer. Suitably, the backing sheet is larger than the active layer such that a marginal region of width 1 mm to 50 mm, suitably 5 mm to 20 mm extends around the active layer to form a so-called island dressing. In such cases, the backing sheet is suitably coated with a pressure sensitive medical grade adhesive in at least its marginal region.

Suitably, the backing sheet is substantially liquid-impermeable. The backing sheet is suitably semipermeable. That is to say, the backing sheet is suitably permeable to water vapour, but not permeable to liquid water or wound exudate. Suitably, the backing sheet is also microorganism-impermeable. Suitable continuous conformable backing sheets will suitably have a moisture vapor transmission rate (MVTR) of the backing sheet alone of 300 to 5000 $g/m^2/24$ hrs, suitably 500 to 2000 $g/m^2/24$ hrs at 37.5° C. at 100% to 10% relative humidity difference. The backing sheet thickness is suitably in the range of 10 to 1000 micrometers, more suitably 100 to 500 micrometers. It has been found that such moisture vapor transmission rates allow the wound under the dressing to heal under moist conditions without causing the skin surrounding the wound to macerate.

Suitable polymers for forming the backing sheet include polyurethanes and poly alkoxyalkyl acrylates and methacrylates such as those disclosed in GB-A-1280631. Suitably, the backing sheet comprises a continuous layer of a high density blocked polyurethane foam that is predominantly closed-cell. A suitable backing sheet material is the polyurethane film available under the Registered Trade Mark ESTANE 5714F.

The adhesive (where present) layer should be moisture vapor transmitting and/or patterned to allow passage of water vapor therethrough. The adhesive layer is suitably a continuous moisture vapor transmitting, pressure-sensitive adhesive layer of the type conventionally used for island-type wound dressings, for example, a pressure sensitive adhesive based on acrylate ester copolymers, polyvinyl ethyl ether and polyurethane as described for example in GB-A-1280631. The basis weight of the adhesive layer is suitably 20 to 250 $g/m^2$, and more suitably 50 to 150 $g/m^2$. Polyurethane-based pressure sensitive adhesives are preferred.

Further layers of a multilayer absorbent article may be built up between the active layer and the protective sheet. For example, these layers may comprise an absorbent layer between the active layer and the protective sheet, especially if the dressing is for use on exuding wounds. The optional absorbent layer may be any of the layers conventionally used for absorbing wound fluids, serum or blood in the wound healing art, including gauzes, nonwoven fabrics, superabsorbents, hydrogels and mixtures thereof. Suitably, the absorbent layer comprises a layer of absorbent foam, such as an open celled hydrophilic polyurethane foam prepared in accordance with EP-A-0541391. In other embodiments, the absorbent layer may be a nonwoven fibrous web, for example a carded web of viscose staple fibers. The basis weight of the absorbent layer may be in the range of 50-500 $g/m^2$, such as 100-400 $g/m^2$. The uncompressed thickness of the absorbent layer may be in the range of from 0.5 mm to 10 mm, such as 1 mm to 4 mm. The free (uncompressed) liquid absorbency measured for physiological saline may be in the range of 5 to 30 g/g at 25°. Suitably, the absorbent layer or layers are substantially coextensive with the active layer.

The wound facing surface of the dressing is suitably protected by a removable cover sheet. The cover sheet is normally formed from flexible thermoplastic material. Suitable materials include polyesters and polyolefins. Suitably, the adhesive-facing surface of the cover sheet is a release surface. That is to say, a surface that is only weakly adherent to the active layer and the adhesive on the backing sheet to assist peeling of the adhesive layer from the cover sheet. For example, the cover sheet may be formed from a non-adherent plastic such as a fluoropolymer, or it may be provided with a release coating such as a silicone or fluoropolymer release coating.

Typically, the wound dressing according to the present invention is sterile and packaged in a microorganism-impermeable container.

In a further aspect, the present invention provides method of treatment of a wound comprising applying thereto an effective amount of a dressing material according to the present invention. Suitably, the treatment comprises applying to said wound a dressing according to the present invention.

The material is suitably applied to the wound for a period of at least about 1 hour, more suitably from about 4 hours to about 4 weeks, for example from about 1 day to about 14 days, optionally with dressing changes during the course of the treatment.

Suitably, the wound is a chronic wound. More suitably, the chronic wound is selected from the group consisting of ulcers, in particular dermal ulcers. For example, venous ulcers, decubitus ulcers, or diabetic ulcers. The wound dressing materials according to the present invention promote collagen synthesis and collagen gel contraction in vitro (see below), which suggests that they may provide advantages in the healing of chronic wounds.

Accordingly, in a further aspect, the present invention provides a material comprising a wound dressing carrier, N-acetyl cysteine or a salt or derivative thereof; and ascorbic acid or a salt or derivative thereof, for use in the treatment of a chronic dermal wound.

Suitably, the carrier, the NAC and the ascorbate are as described above in relation to the first aspect of the invention.

Where present, the ascorbic acid or salts thereof are used in similar amounts to the amounts of the stabilized ascorbate used in the embodiments according to the first aspect.

In a further aspect, the present invention provides a method of making a wound dressing material comprising the steps of:
(a) dispersing one or more medically acceptable polymeric materials, N-acetyl cysteine or a salt or derivative thereof, and ascorbic acid or a salt or derivative thereof in an aqueous solvent to form an aqueous dispersion; and
(b) freeze-drying or solvent-drying the aqueous dispersion to produce the wound dressing material.

Suitably, the method according to this aspect of the invention is a method of making a wound dressing material according to the first or second aspects of the invention.

The polymeric materials are suitably as described above in relation to the first aspect of the present invention. Suitably, the dispersion has a solids concentration of from about 0.5% to about 3% by weight.

Suitably, the dispersion has a pH of from about 3 to about 4. Where a derivative such as ascorbate 2-polyphosphate that has low solubility are used, conventional acidifying agents such as acetic acid are used to achieve the desired pH.

Suitably, the dispersion comprises from about 0.0002% to about 1% by weight of the NAC, salt or derivative thereof, for example from about 0.03% to about 0.4%, typically about 0.05% to about 0.3%, based on the weight of the dispersion. Suitably, the dispersion comprises from about 0.0002% to about 1% by weight of the ascorbic acid, salt or derivative thereof, for example from about 0.03% to about 0.4%, typically about 0.05% to about 0.3%, based on the weight of the dispersion.

The method according to this aspect of the invention further comprises freeze-drying or solvent-drying the dispersion. Freeze-drying comprises the steps of freezing the dispersion, followed by evaporating the solvent from the frozen dispersion under reduced pressure. Suitably, the method of freeze-drying is similar to that described for a collagen-based sponge in U.S. Pat. No. 2,157,224. Solvent drying comprises freezing the dispersion, followed by immersing the frozen dispersion in a series of baths of a hygroscopic organic solvent such as anhydrous isopropanol to extract the water from the frozen dispersion, followed by removing the organic solvent by evaporation. Methods of solvent drying are described, for example, in U.S. Pat. No. 3,157,524.

In certain embodiments the process may further comprise treating the dispersion, or the dried material, with a cross-linking agent such as epichlorhydrin, carbodiimide, hexamethylene diisocyanate (HMDI) or glutaraldehyde. Alternatively, cross-linking may be carried out dehydrothermally. The method of cross-linking can markedly affect the final product. For example, HMDI cross-links the primary amino groups on collagen, whereas carbodiimide cross-links carbohydrate on the ORC to primary amino groups on the collagen.

Especially suitable methods of making freeze-dried and solvent-dried sponges are described in EP-A-1153622 and EP-A-0838491.

It will be appreciated that any feature or embodiment that is described herein in relation to any one aspect of the invention may also be applied to any other aspect of the invention.

Specific embodiments of the invention will now be described further, by way of example, with reference to the accompanying drawings, in which.

Figure 1:
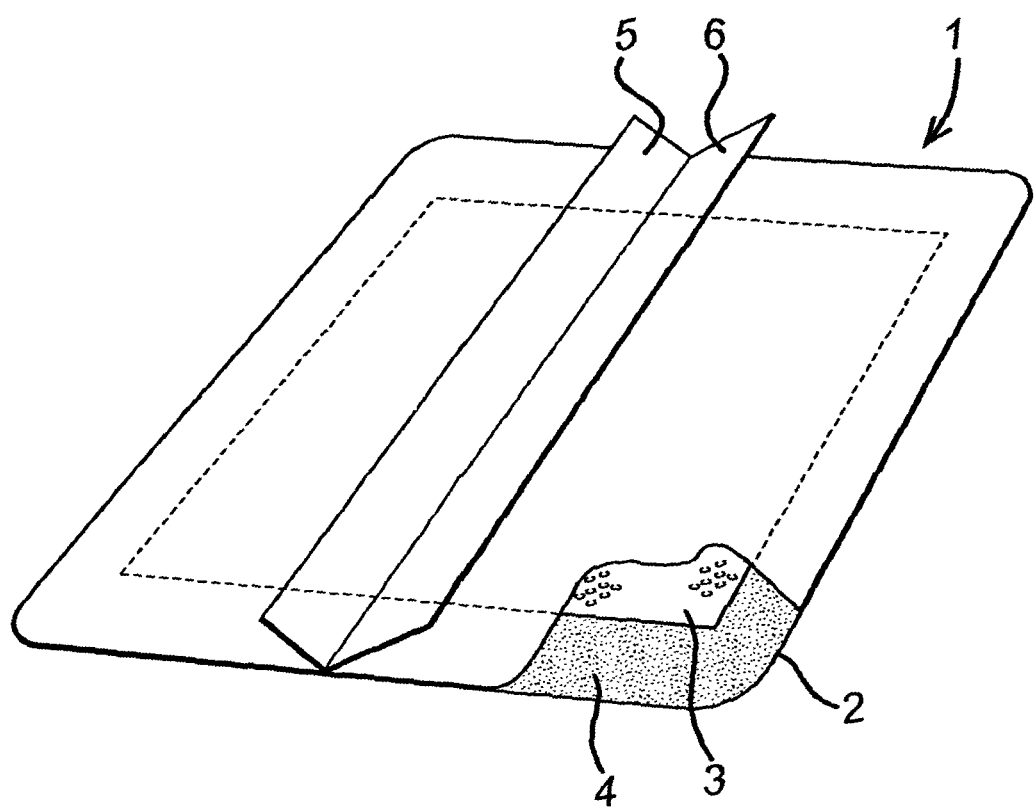
FIG. 1 shows a wound dressing according to the present invention incorporating a sheet of the material according to the invention.

Referring to FIG. 1, a wound dressing 1 according to the present invention is an island-type, self-adhesive wound dressing comprising a backing layer 2 of microporous liquid-impermeable polyurethane foam. The backing layer 2 is permeable to water vapor, but impermeable to wound exudate and microorganisms.

The backing layer is coated with a substantially continuous layer of pressure-sensitive polyurethane adhesive. A rectangular island 3 of a wound dressing material according to the invention in sheet form, made in accordance with Example 1 below, is adhered to a central region of the adhesive-coated backing sheet 2 such that an adhesive-coated margin 4 of the backing sheet extends around the island for attachment of the dressing to the skin around a wound.

The dressing further comprises protective, release-coated cover sheets 5,6. These cover sheets are removed immediately before use of the dressing. The dressing is suitably sterile and packaged in a microorganism-impermeable pouch (not shown) prior to use.

EXAMPLE 1

A collagen/ORC sponge containing NAC and AZP was prepared by a modification of the method for the preparation of Collagen/ORC sponges described in Example 1 of EP-A-1153622.

Briefly, the collagen component is prepared from bovine corium as follows. Bovine corium is split from cow hide, scraped and soaked in sodium hypochlorite solution (0.03% w/v) to inhibit microbial activity pending further processing. The corium is then washed with water and treated with a solution containing sodium hydroxide (0.2% w/v) and hydrogen peroxide (0.02% w/v) to swell and sterilize the corium at ambient temperature. The corium splits then undergo an alkali treatment step in a solution containing sodium hydroxide, calcium hydroxide and sodium bicarbonate (0.4% w/v, 0.6% w/v and 0.05% w/v, respectively) at pH greater than 12.2, ambient temperature, and for a time of 10-14 days, with tumbling, until an amide nitrogen level less than 0.24 mmol/g is reached. The corium splits then undergo an acid treatment step with 1% hydrochloric acid at ambient temperature and pH 0.8-1.2. The treatment is continued with tumbling until the corium splits have absorbed sufficient acid to reach a pH less than 2.5. The splits are then washed with water until the pH value of corium splits reaches 3.0-3.4. The corium splits are then comminuted with ice in a bowl chopper first with a coarse comminution and then with a fine comminution setting. The resulting paste, which is made up in a ratio of 650 g of the corium splits to 100 g of water, as ice, is frozen and stored before use in the next stage of the process. However, the collagen is not freeze-dried before admixture with the ORC in the next stage.

The ORC component of the freeze-dried pad is prepared as follows. A SURGICEL cloth (Johnson & Johnson Medical, Arlington) is milled using a rotary knife cutter through a screen-plate, maintaining the temperature below 60° C.

The milled ORC powder and the required weight (according to solids content) of frozen collagen paste are then added to a sufficient amount of water acidified with acetic acid to form an aqueous dispersion. NAC and Ascorbate 2-triphosphate (STAY-C, Roche) are each dissolved into the aqueous acetic acid prior to addition of the ORC and collagen, to give a final concentrations of NAC of 4.5 mM and a final concentration of ascorbate 2-triphosphate of 4.5 mM. The resulting aqueous dispersion has pH value of 3.0 and a total solids content of 2.0% (note: the method of Example 1 of EP-A-1153622 uses a 1% solids slurry). The mixture is homogenized through a Fryma MZ130D homogenizer, progressively diminishing the settings to form a homogeneous slurry. The pH of the slurry is maintained at 2.9-3.1. The slurry temperature is maintained below 20° C., and the solids content is maintained at 2%±0.07. Surprisingly, it was found that the slurry having this higher solids content has a sufficiently low viscosity for handling in the subsequent stages of the process.

The resulting slurry is pumped to a degassing vessel. Vacuum is initiated for a minimum of 30 minutes, with intermittent stirring, to degas the slurry. The slurry is then pumped into freeze-drier trays to a depth of 25 mm. The trays are placed onto freezer shelves where the temperature has been preset to −40° C. The freeze-drier programme is then initiated to dry and dehydrothermally cross-link the collagen and ORC to form thick sponge pads. On completion of the cycle, the vacuum is released, the freeze-dried blocks are removed, and are then split to remove the top and bottom surface layers, and to divide the remainder of the blocks into 3 mm-thick pads. The step of splitting the freeze-dried blocks into pads is carried out with a Fecken Kirfel K1 slitter. Finally, the pads are die-cut to the desired size and shape on a die-cutter, packaged, and sterilized with 18-29 KGy of cobalt 60 gamma-irradiation. Surprisingly, this irradiation does not cause significant denaturation of the collagen, which appears to be stabilized by the presence of ORC. The resulting freeze-dried collagen ORC pads have a uniform, white, velvety appearance. The thickness of the pads is 3.2±0.17 mm (N=8 batches).

EXAMPLE 2

The procedure of Example 1 was repeated, but with addition of NAC and ascorbate-2-triphosphate in amounts of 2.5 mM and 2.5 mM respectively to the slurry.

EXAMPLE 3

The procedure of Example 1 was repeated, but with addition of NAC and ascorbate-2-triphosphate in amounts of 0.5 mM and 0.5 mM respectively to the slurry.

REFERENCE EXAMPLES 4-9

Reference sponges were prepared by the method of Example 1 with the following actives in the slurry in the following amounts:
Reference Example 4: NAC 1 mM
Reference Example 5: NAC 5 mM
Reference Example 6: NAC 9 mM
Reference Example 7: ascorbate-2-triphosphate 1 mM
Reference Example 8: ascorbate-2-triphosphate 5 mM
Reference Example 9: ascorbate-2-triphosphate 9 mM Procedure 1: Measurement of Collagen Synthesis by Dermal Fibroblasts A collagen synthesis assay with dermal fibroblasts was performed. This is standard assay which shows the amount of collagen synthesised by fibroblasts after stimulation with the active agents.

Briefly, the collagen synthesis assay involved plating 8.4× $10^4$ human fibroblasts (per well) into 24-well plates, and incubating them at 37° C., 5% $CO_2$, in 10% FBS-DMEM. Once cells were confluent (within 24 hours of plating), the 10% FBS-DMEM was removed, cells washed 3× with SF-DMEM, before a SF-DMEM extract of the sponge samples of Examples 1-9 was added to the cells. Cells were incubated for 72 hours after which time the media were collected. A commercial immunoassay (Metra-CICP Kit, Quidel, San Diego, USA) was used that measured the level of C-terminal propeptide of Type-1 Collagen (CICP) present in the cell culture media. The level of CICP in the media, which is released by the fibroblasts as a by-product of collagen synthesis, is proportional to the level of collagen synthesis and so its level was used to determine the level of collagen synthesis.

Figure 2:
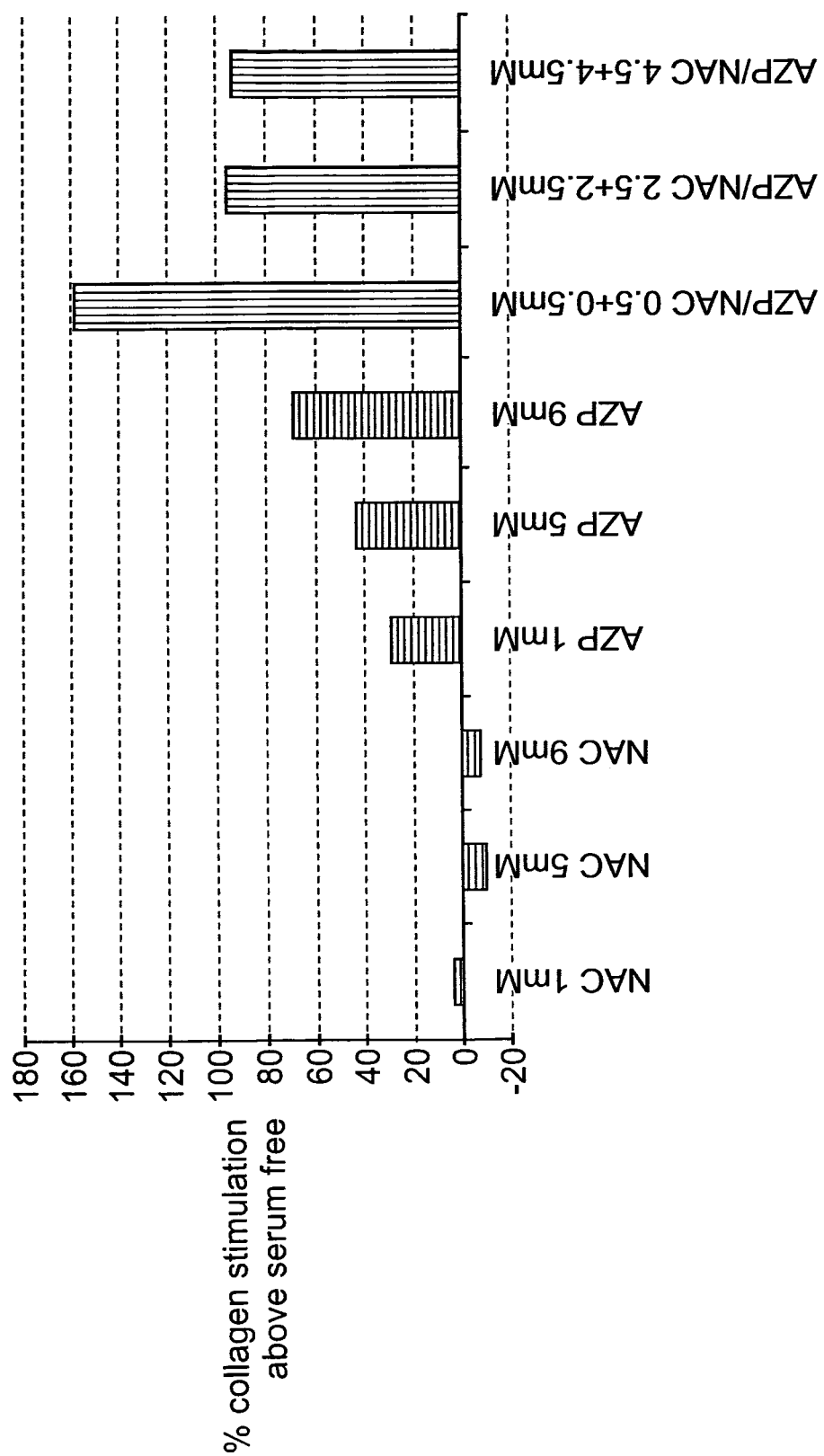
FIG. 2 shows the percentage stimulation of collagen synthesis in dermal fibroblast cells measured by Procedure 1 for the examples and reference examples.
Figure 3:
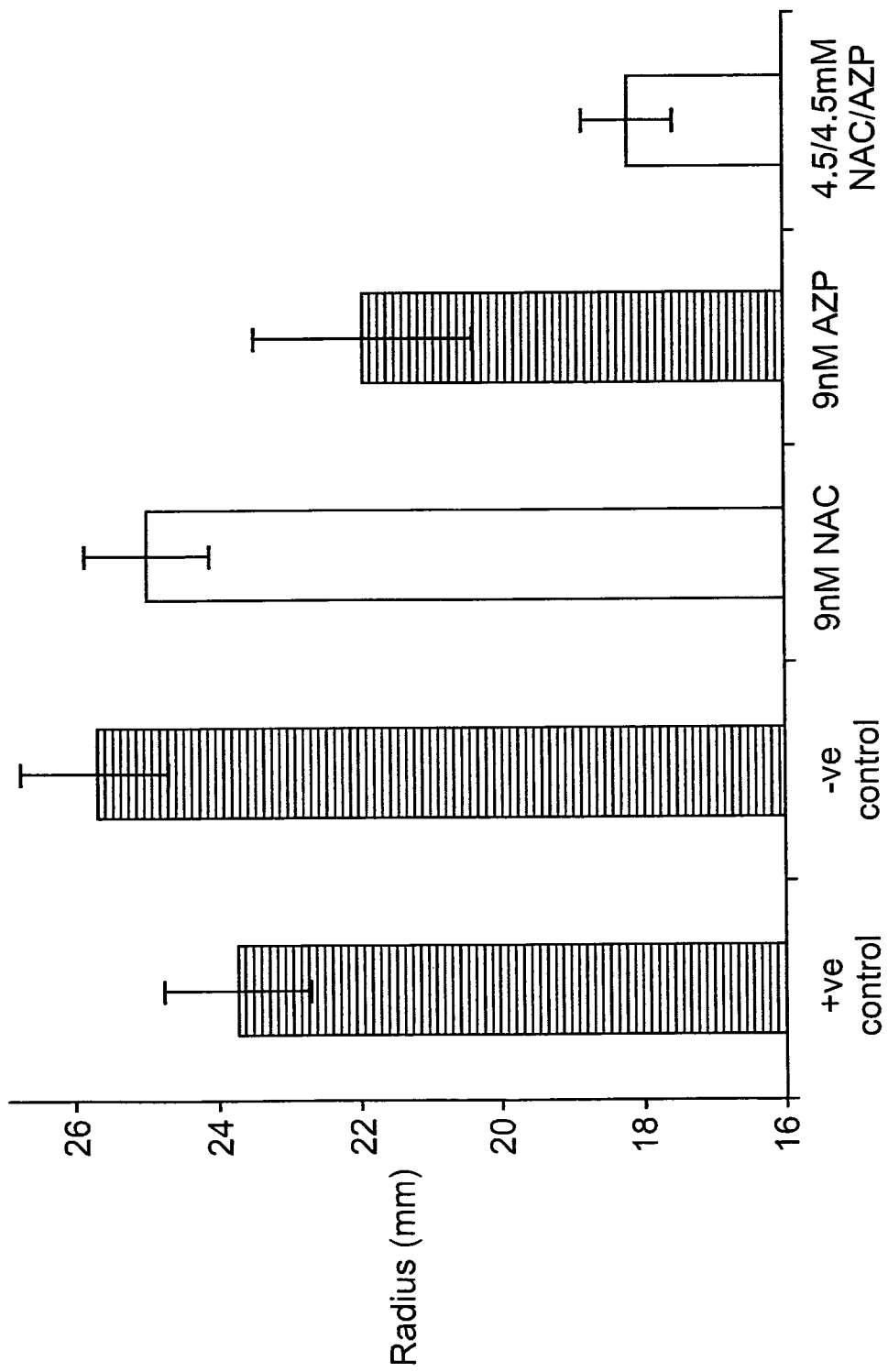
FIG. 3 shows the observed radius of the collagen sheet in the gel contraction measurement according to Procedure 2 for certain examples and reference examples.

The results are shown graphically in FIG. 2. It can be seen that the combination of ascorbate-2-triphosphate with NAC gives a synergistic improvement in collagen synthesis. This is expected to result in improved wound healing in vivo, in particular for chronic wounds.

Procedure 2: Measurement of Collagen Gel Contraction

The measurement of collagen gel contraction, performed in vitro, gives a good indication of the ability of actives to promote cellular response. The procedure was as follows:

1. Normal human dermal fibroblasts were maintained in 10% FBS/DMEM (Fetal bovine serum & Dulbecco's minimally modified medium), and grown in a humidified incubator containing 5% $CO_2$. Cells were split at 95% confluency and were used for experiments when approx. 90% confluent.
2. Cells were harvested using 0.05% trypsin/EDTA (GIBCO BRL), counted using a haemocytometer and centrifuged to obtain cell pellet.
3. Cells were then resuspended at a cell density of 140,000 cells/ml—4 times the final cell density in the collagen gel.
4. The following cell/collagen mixture was prepared for each 24-well plate:
14 mls 10% FBS/DMEM
7 mls cells at 140,000 cells/ml
7 mls soluble collagen—rat tail type I collagen from Collaborative Biomedical (supplied by Fred Baker Scientific: 356236)—final concentration 1 mg/ml—it is usually supplied at approx. 4 mg/ml thus 7 mls was taken directly from the bought stock solution.

This mixture was then distributed at 1 ml/well into each of a 24-well tissue culture plate, and allowed to gel for 1 hr at 37° C.

5. Once the gels had polymerized they were rimmed with a sterile pipette tip and an additional 0.5 ml of medium added carefully to each well. This additional medium contained the test reagent (at 3 times the final required concentration to account for dilution).

The plates were photographed and then incubated at 37° C. in 5% $CO_2$ in a humid environment. Photographs were taken at similar times each day until the end of the experiment—usually day 14 or 15 after setup. At day four the measurements of each well for each test substance were averaged and were compared to each other and to the control. A faster the rate of contraction was indicated by a reduction in diameter of the gel.

Collagen gel contractions were prepared and incubated over four days with the following solutions. Positive control; 10% FBS DMEM—Negative control; Serum Free DMEM. Test Solutions, 9 mM AZP, 9 mM NAC, 9 mM AZP/NAC combination and 4.5 mM NAC/AZP combination.

The results show that a faster rate of contraction is achieved with the 4.5 mM AZP/NAC combination that with any other solution. This is a faster rate than the ascorbate-2-triphosphate or the NAC on their own and is faster than the positive control. This indicates that this level of active is optimal for the contraction of collagen and proliferation of the dermal fibroblasts.

All patent applications referred to herein are expressly incorporated in their entirety.

The above examples have been described for the purpose of illustration only. Many other embodiments falling within the scope of the accompanying claims will be apparent to the skilled reader.

The invention claimed is:

1. A wound dressing material comprising:
   a wound dressing carrier;
   N-acetyl cysteine or a salt or derivative thereof; and
   a stabilized ascorbate;
   wherein the weight ratio of N-acetyl cysteine or a salt or derivative thereof to said stabilized ascorbate is from about 1:4 to about 4:1; and
   wherein said stabilized ascorbate comprises ascorbate-2-triphosphate.

2. A wound dressing material according to claim 1, wherein the material comprises from about 0.1 wt. % to about 20 wt. % of said N-acetyl cysteine or salts or derivatives thereof, and from about 0.1 wt. % to about 20 wt. % of said stabilized ascorbate.

3. A wound dressing material according to claim 2, wherein the material comprises from about 1 wt. % to about 10 wt. % of said N-acetyl cysteine or salts or derivatives thereof, and from about 1 wt. % to about 10 wt. % of said stabilized ascorbate.

4. A wound dressing material according to claim 1, wherein the material comprises N-acetyl cysteine and ascorbate-2-triphosphate.

5. A wound dressing material according to claim 1, wherein the carrier comprises a woven or nonwoven fabric, a foam, a freeze-dried or solvent-dried sponge, or a solid film.

6. A wound dressing material according to claim 1, wherein the wound dressing carrier is bioabsorbable.

7. A wound dressing material according to claim 1, wherein the carrier comprises a freeze-dried or solvent-dried sponge, and said sponge carrier comprises oxidized cellulose, optionally in combination with collagen or chitosan.

8. A method for treatment of a chronic dermal wound, comprising:
   providing a wound dressing wherein the wound dressing comprises a wound dressing carrier, and in the carrier a N-acetyl cysteine or a salt or derivative thereof and stabilized ascorbate; and
   applying the wound dressing to the chronic dermal wound;
   wherein the weight ratio of N-acetyl cysteine or a salt or derivative thereof to said stabilized ascorbate is from about 1:4 to about 4:1; and
   wherein said stabilized ascorbate comprises ascorbate-2-triphosphate.

9. A wound dressing comprising a wound dressing material comprising:
   a wound dressing carrier;
   N-acetyl cysteine or a salt or derivative thereof; and
   a stabilized ascorbate;
   wherein the weight ratio of N-acetyl cysteine or a salt or derivative thereof to said stabilized ascorbate is from about 1:4 to about 4:1;
   wherein said stabilized ascorbate comprises ascorbate-2-triphosphate.

10. A wound dressing according to claim 9 which is sterile and packaged in a microorganism-impermeable container.

11. A method of treatment of a wound comprising applying to the wound a wound dressing comprising a wound dressing material comprising:
    a wound dressing carrier;
    N-acetyl cysteine or a salt or derivative thereof; and
    a stabilized ascorbate;
    wherein the weight ratio of N-acetyl cysteine or a salt or derivative thereof to said stabilized ascorbate is from about 1:4 to about 4:1; and
    wherein said stabilized ascorbate comprises ascorbate-2-triphosphate.

12. A method of making a wound dressing material comprising the steps of:
    (a) dispersing one or more medically acceptable polymeric materials, N-acetyl cysteine or a salt or derivative thereof, and ascorbic acid or a salt or derivative thereof in an aqueous solvent to form an aqueous dispersion; and
    (b) freeze-drying or solvent-drying the aqueous dispersion to produce the wound dressing material;
    wherein the weight ratio of N-acetyl cysteine or a salt or derivative thereof to said ascorbic acid or a salt or derivative thereof is from about 1:4 to about 4:1; and
    wherein said stabilized ascorbate comprises ascorbate-2-triphosphate.

13. The method of claim 8, wherein the wound dressing comprises from about 0.1 wt. % to about 20 wt. % of said N-acetyl cysteine or salts or derivatives thereof, and from about 0.1 wt. % to about 20 wt. % of said stabilized ascorbate.

14. The method of claim 8, wherein the carrier comprises a woven or nonwoven fabric, a foam, a freeze-dried or solvent-dried sponge, or a solid film.

15. The wound dressing material of claim 1, wherein the carrier is bioabsorbable and provides sustainable release of ascorbic acid and N-acetyl cysteine to a wound.

16. A wound dressing according to claim 9, wherein the wound dressing carrier is bioabsorbable.

17. A wound dressing according to claim 9, wherein the material comprises from about 1 wt. % to about 10 wt. % of said N-acetyl cysteine or salts or derivatives thereof, and from about 1 wt. % to about 10 wt. % of said stabilized ascorbate.

18. A wound dressing according to claim 17, wherein the carrier consists essentially of a freeze-dried sponge, or a solvent-dried sponge.

19. A wound dressing material according to claim 18, wherein the wound dressing carrier is bioabsorbable.

20. A wound dressing according to claim 18, wherein said sponge carrier comprises oxidized cellulose, in combination with collagen or chitosan.

* * * * *